(12) United States Patent
Harui et al.

(10) Patent No.: US 7,610,942 B2
(45) Date of Patent: Nov. 3, 2009

(54) CELL SUSPENSION ROTATING FLUIDIC PUMP

(75) Inventors: Norio Harui, Seattle, WA (US); Michael A. Crawford, Auburn, WA (US); Richard J. Esposito, Seattle, WA (US); William E. Ortyn, Bainbridge Island, WA (US)

(73) Assignee: Amnis Corporation, Seattle, WA (US)

( * ) Notice: Subject to any disclaimer, the term of this patent is extended or adjusted under 35 U.S.C. 154(b) by 1154 days.

(21) Appl. No.: 10/757,971

(22) Filed: Jan. 15, 2004

(65) Prior Publication Data

US 2004/0220472 A1 Nov. 4, 2004

Related U.S. Application Data

(60) Provisional application No. 60/440,417, filed on Jan. 15, 2003.

(51) Int. Cl.
*B65B 1/20* (2006.01)
*G01N 35/00* (2006.01)

(52) U.S. Cl. ............... 141/11; 141/69; 366/213; 436/43

(58) Field of Classification Search ............ 141/1, 141/2, 11, 25–27, 69, 271; 366/200, 213; 604/181; 436/43
See application file for complete search history.

(56) References Cited

U.S. PATENT DOCUMENTS

| | | | | |
|---|---|---|---|---|
| 3,542,344 A | * | 11/1970 | Oberhauser | 366/202 |
| 3,922,069 A | | 11/1975 | Kishikawa et al. | 359/633 |
| 4,040,940 A | | 8/1977 | Bier | 204/299 R |
| 4,235,553 A | * | 11/1980 | Gall | 366/208 |
| 4,390,283 A | * | 6/1983 | Meyer | 366/142 |
| 4,461,578 A | * | 7/1984 | Tiebout | 366/213 |
| 4,635,293 A | | 1/1987 | Watanabe | 382/130 |
| 4,677,680 A | | 6/1987 | Harima et al. | 382/112 |
| 4,988,623 A | | 1/1991 | Schwarz et al. | 435/286 |
| 5,026,650 A | | 6/1991 | Schwarz et al. | 435/286 |
| 5,034,004 A | | 7/1991 | Crankshaw | 604/154 |
| 5,104,802 A | | 4/1992 | Rhodes et al. | 435/286 |
| 5,141,609 A | | 8/1992 | Sweedler et al. | 204/452 |

(Continued)

OTHER PUBLICATIONS

Hecht, Eugene. "Optics $4^{th}$ ed." 2002. Addison-Wesley Longman, Inc., XP-002465391. ISBN: 0-8053-8566-5.

(Continued)

*Primary Examiner*—Timothy L Maust
(74) *Attorney, Agent, or Firm*—Ronald M. Anderson

(57) ABSTRACT

A low pulsatility syringe pump including a duplex bearing set rotatingly supporting a lead screw, and a transmission having a first drive train configured to increase a number of motor rotations required for a single rotation of the lead screw, and a second drive train configured to reduce the number of motor rotations required for a single rotation of the lead screw as compared to the first drive train. Another embodiment also includes a motor configured to rotate the syringe about its own axis, independent of the motion of the lead screw. In this other embodiment, the fluid in the syringe barrel includes objects (such as cells, latex beads, etc.) entrained in the fluid. The rate of rotation (e.g., about three revolutions per second) is chosen such that each object traces a substantially circular pathway in the syringe barrel and remains in suspension.

11 Claims, 4 Drawing Sheets

U.S. PATENT DOCUMENTS

| | | | |
|---|---|---|---|
| 5,153,131 A | 10/1992 | Wolf et al. | 435/240.24 |
| 5,153,132 A | 10/1992 | Goodwin et al. | 435/240.24 |
| 5,153,133 A | 10/1992 | Schwarz et al. | 435/240.24 |
| 5,153,916 A | 10/1992 | Inagaki et al. | 382/151 |
| 5,155,034 A | 10/1992 | Wolf et al. | 435/240.24 |
| 5,155,035 A | 10/1992 | Schwarz et al. | 435/240.24 |
| 5,167,448 A * | 12/1992 | Herold et al. | 366/213 |
| 5,176,646 A | 1/1993 | Kuroda | 604/154 |
| 5,219,099 A | 6/1993 | Spence et al. | 222/325 |
| 5,330,908 A | 7/1994 | Spaulding | 435/240.24 |
| 5,351,311 A | 9/1994 | Rogers | 382/156 |
| 5,355,373 A * | 10/1994 | Salmon et al. | 310/71 |
| 5,399,013 A * | 3/1995 | Sawyer | 366/211 |
| 5,499,872 A * | 3/1996 | Baxter | 366/213 |
| 5,511,880 A * | 4/1996 | Macemon | 366/213 |
| 5,548,349 A | 8/1996 | Mizuguchi et al. | 348/766 |
| 5,568,315 A | 10/1996 | Shuman | 359/487 |
| 5,754,291 A | 5/1998 | Kain | 356/338 |
| 5,760,899 A | 6/1998 | Eismann | 356/326 |
| 5,911,252 A | 6/1999 | Cassel | 141/234 |
| 6,080,581 A | 6/2000 | Anderson et al. | 435/394 |
| 6,330,361 B1 | 12/2001 | Mitchell et al. | 382/211 |
| 6,387,077 B1 * | 5/2002 | Klibanov et al. | 604/181 |
| 6,428,517 B1 | 8/2002 | Hochman et al. | 604/188 |
| 6,431,745 B1 * | 8/2002 | Schlumberger | 366/211 |
| 6,549,664 B1 | 4/2003 | Daiber et al. | 382/232 |
| 6,554,792 B2 | 4/2003 | Hughes | 604/85 |
| 6,575,930 B1 | 6/2003 | Trombley, III et al. | 604/82 |
| 6,640,840 B1 * | 11/2003 | MacNeil | 141/1 |
| 6,657,713 B2 * | 12/2003 | Hansen | 356/237.1 |
| 6,763,149 B2 | 7/2004 | Riley et al. | 382/294 |
| 7,006,710 B2 | 2/2006 | Riley et al. | 382/294 |
| 2004/0027914 A1 * | 2/2004 | Vrane | 366/213 |

OTHER PUBLICATIONS

Robert, G.O., Kornfeld, D.M. and Fowlis, W.W., Particle Orbits in a Rotating Liquid, "*Journal of Fluid Mechanics*," 1991. vol. 229, pp. 555-567.

* cited by examiner

US 7,610,942 B2

CELL SUSPENSION ROTATING FLUIDIC PUMP

RELATED APPLICATION

This application is based on prior provisional patent application Ser. No. 60/440,417, filed on Jan. 15, 2003, the benefit of the filing date of which is hereby claimed under 35 U.S.C. § 119(e).

FIELD OF THE INVENTION

The present invention generally relates to a method and apparatus for dispensing particles that are in a liquid suspension, and more specifically, to the precise and accurate introduction of a liquid sample and the controlled suspension of particles in the liquid sample.

BACKGROUND OF THE INVENTION

A flow cytometer is used for studying particles, such as cells and latex beads, which are suspended in a liquid stream that is passed through an imaging apparatus for a prolonged time. Recently, an imaging flow cytometer technology, termed ImageStream™, has been developed for evaluating cells and other that are conveyed through an imaging apparatus. These significant advancements in the art of flow cytometry are described in commonly assigned U.S. Pat. No. 6,249,341, issued on Jun. 19, 2001 and entitled IMAGING AND ANALYZING PARAMETERS OF SMALL MOVING OBJECTS SUCH AS CELLS, as well as in commonly assigned U.S. Pat. No. 6,211,955 issued on Apr. 3, 2001, also entitled IMAGING AND ANALYZING PARAMETERS OF SMALL MOVING OBJECTS SUCH AS CELLS, as well as commonly assigned U.S. Pat. No. 6,473,176, issued on Oct. 29, 2002, and also entitled IMAGING AND ANALYZING PARAMETERS OF SMALL MOVING OBJECTS SUCH AS CELLS. The specifications and drawings of each of these patents are hereby specifically incorporated herein by reference.

In a manner similar to a conventional flow cytometer, an ImageStream™ imaging flow cytometer uses hydrodynamic focusing to confine a sample core fluid containing cells of interest to a central portion of a flowing stream of a cell-free sheath fluid. Sheath flow improves the precision with which the cell sample can be positioned in an observation region of the cytometer by restricting the cells to the central region of the stream. An additional advantage of using sheath flow is that it reduces the possibility of clogging in the fluidic system. By using sheath flow, a typical core flow diameter of about 10 microns and a sheath flow diameter of about 200 microns are achieved. Without the use of sheath flow, the flow cell would need to be restricted to about 10 microns in diameter, thus allowing particles of about 10 microns or greater in size to obstruct the fluidic system.

Currently, most flow cytometers employ gas pressure to inject the core and sheath streams. The gas pressure injection is accomplished by connecting a sample vial containing the liquid sample to the fluidic system via an o-ring seal, and inserting two fluid lines into the sample vial. The first fluid line is a gas pressure fluid line, which is generally coupled in fluid communication with the head space of the sample vial. The second fluid line is disposed adjacent the bottom of the sample vial. As the pressure is increased in the head space of the sample vial, the liquid sample is forced into the second fluid line, so that the liquid sample is removed from the sample vial.

Such a conventional pressurized gas injection technique is inadequate for the recently developed ImageStream™ imaging flow cytometer for at least two reasons. First, the low flow rates used in the ImageStream™ system would require very low gas pressures, which are quite challenging to regulate accurately. Second, such gas systems are constant pressure systems, which are prone to clogging. A more preferred injection system employs constant volume pumping, such as provided by syringe pumps.

One example of a syringe pump is disclosed in U.S. Pat. No. 5,176,646 (Kuroda), which describes a single speed syringe pump using a stepping motor and implemented with a plurality of belts and pulleys, providing a low cost alternative to more expensive syringe pumps that include precision machined lead screws. For example, U.S. Pat. No. 5,219,099 (Spence et al.) discloses a syringe pump that uses a stepping motor to rotate a lead screw with precision. The syringe barrel, plunger, and stepper motor drive shaft are all coaxially aligned with the syringe barrel axis in order to eliminate all forces that are not coaxially aligned.

However, existing syringe pumps suffer from pulsatility issues and a general inability to offer both precisely controlled delivery of small volumes of fluid, as well as the inability to rapidly reload the fluid reservoir of the syringe. Pulsatility refers to the introduction of rhythmic or irregular pulses into a flow of fluid discharged by a fluid delivery system. Particularly with respect to the delivery of small volumes of fluid, such pulsatility is undesirable. It would therefore be desirable to provide new method and apparatus for the delivery of small volumes of fluid to enable the fluid to be delivered at a constant volume with low pulsatility, while enabling a uniform suspension of cells, beads, or other particles of interest in the sample fluid, and enabling the rapid reloading of the source syringe—all without sacrificing the ability to accurately deliver small volumes of fluid.

The pulsatility issue is particularly important in an imaging flow cytometer. The ImageStream™ optical imaging flow cytometer system, as described in commonly owned U.S. Pat. No. 6,249,341 (Basiji et al.) and U.S. Pat. No. 6,211,955 (Basiji et al.) provides high resolution, high sensitivity two-dimensional (2D) and three-dimensional (3D) imaging using time-delay-integration (TDI) electronic image acquisition of cells in flow. These instruments are designed to expand the analysis capabilities of biological specimens in fluid suspensions beyond the limits of conventional flow cytometers. TDI sensors use solid-state photon detectors, such as charge-coupled device (CCD) arrays and shift lines of photon-induced charge in the arrays in synchronization with the flow of the particle of interest. The method enables a long exposure time that increases the signal-to-noise ratio (SNR) in the image, while minimizing blurring. Precise synchronization of the TDI detector timing with the motion of the moving targets is required for blurring of the resulting images to be eliminated or minimized. For example, if a target traverses 512 lines of a TDI sensor to build an image, and blurring of less than a single line width is desired, the velocity of the target must be known with a maximum permissible error of less than 0.2 percent.

To synchronize the TDI detector read out rate with the sample, a novel velocity detection method and apparatus has been developed. Commonly assigned U.S. patent application Ser. Nos. 09/939,292 and 09/939,049, both entitled MEASURING THE VELOCITY OF SMALL MOVING OBJECTS SUCH AS CELLS, describe a method and apparatus for determining a particle's velocity with a high degree of precision. These specification and drawings of both these applications are hereby specifically incorporated herein by reference. Light from an object entrained in the sample liquid core of the flow cell is modulated via an optical grating. The modulated light is detected and analyzed either in the time or frequency domain to determine the velocity of the object.

The velocity detection and synchronization method and apparatus disclosed in the above-identified patent applications are preferably implemented at a rate of approximately five times per second, enabling the determination of velocity to within 1 part in 1000. Such an implementation is adequate for relatively low frequency changes in cell flow speed (i.e., <5 Hz); however, it is not adequate for high frequency oscillations in cell velocity (i.e., where pulsatility in fluid flow exists). While low frequency changes in flow velocity can be compensated by using the velocity detection and synchronization method and apparatus disclosed in the above-identified patent applications, such velocity variations effectively decrease the maximum throughput flow velocity of the system, since the system must operate at speeds lower or equal to the maximum TDI detector read-out rate. Therefore, if the system has a high variation in low frequency velocity, the average velocity must be decreased so as not to surpass the TDI detector read-out rate. Therefore, it would be desirable to provide a fluidic pump that has a low degree of pulsatility.

In a current implementation of the aforementioned ImageStream™ system, sample analysis rates range from about 100 to about 5,000 cells per second. The maximum rate thus achieved is not as high as is employed in conventional flow cytometers, which often have sample rates ranging from about 10,000 to about 100,000 cells per second. Moreover, because of the use of a TDI detector in the aforementioned ImageStream™ system, the analysis time for samples analyzed in an ImageStream™ system is actually much longer than in conventional cytometers. Analysis times of up to 20 minutes or longer, which can provide greater accuracy, can be achieved using an ImageStream™ system. Given such lengthy analysis times, it is likely that if the sample were not mixed or agitated occasionally, the concentration of the sample fluid would not be uniform (i.e., some particles or cells would settle towards the bottom of the sample vessel). Such settling is undesirable, and would result in fluidic sample streams that were not representative of the particle concentration of the original sample being analyzed. Furthermore, in some assays, the concentration of particles can be chosen in order to optimize the analysis rate (cells/second), and such settling would interfere with the optimization. Also, some samples will likely include mixtures of cells or particles having different densities (e.g., whole blood includes different types of cells having different densities), and the different densities would result in some cells or particles settling out more rapidly than others, thereby undesirably distorting the analytical results achieved.

Particles and cells entrained in a fluid become distributed in a non uniform fashion due to the effect of gravity on the particles and cells. Research into the effects of gravity in such cases has resulted in the development of a technique for simulating the effect of microgravity on fluids. In the simulation, a sample container is rotated about its axis, so that the contents of the sample container are exposed to a uniformly varying simulated gravitational field, as opposed to a stationary gravitational field. U.S. Pat. No. 5,104,802 (Rhodes et al.) describes a clinostat for simulating microgravity. In this patent, cells are introduced into a hollow fiber, and the ends of the fiber are sealed with wax. This fiber is porous and is placed into a glass tube that contains a culture media. The fiber and tube are rotated about the longitudinal axis of the tube, which is horizontal, to simulate microgravity during cellular growth.

Rotation of a fluid has also been employed to minimize convective effects in the fluid. U.S. Pat. No. 4,040,940 (Bier) discloses an electrophoretic separation apparatus for soluble or particulate ionized matter. A tube is rotated about its longitudinal axis, while horizontal, to effectively continuously change the gravity vector, which minimizes gross convective effects that can interfere with the electrophoretic separation process. An anode and cathode are placed on separate ends of the separation tube, and a buffer is introduced on the cathode side of the tube while a perpendicular elution stream is provided to enable the collection of separation fractions.

U.S. Pat. No. 5,026,650 (Schwarz et al.) discloses rotating a horizontally disposed cylindrical cell culture vessel for optimizing cell growth. Delicate mammalian cells are uniformly suspended via the rotating culture vessel without turbulent action which can harm the cells. Other similar rotating vessels for cell culture include U.S. Pat. No. 5,155,035 (Schwarz et al.), U.S. Pat. No. 5,155,034 (Wolf et al.), U.S. Pat. No. 5,153,133 (Schwarz et al.), U.S. Pat. No. 5,153,131 (Wolf et al.), U.S. Pat. No. 4,988,623 (Schwarz et al.), U.S. Pat. No. 5,153,132 (Goodwin et al.), and U.S. Pat. No. 6,080,581 (Anderson et al). The disclosure and drawings of these patents are hereby also specifically incorporated herein by reference. A paper entitled "Particle Orbits in a Rotating Liquid" by William W. Fowlis and Dale M. Kornfeld published in the *Journal of Fluid Mechanics*, 1991 describes the difficulty experienced by researchers in producing latex microspheres greater than three microns. Such particles either settled or creamed/floated to the surface as a result of their buoyancy because they are lower in density than the surrounding medium. Prior art agitation devices such as paddle or propeller-type stirrers resulted in aggregation or flocculation of particles during the latex bead polymerization reaction. In light of these difficulties, such large diameter particles were only successfully manufactured in space, in experiments performed on the U.S. Space Shuttle, since the micro-gravity environment provided there enabled the beads to be suspended uniformly during polymerization.

An earth-bound rotary reactor was later developed to achieve a similar suspension in a gravity environment. By slowly rotating the vessel, the fluid contents begin to turn as a solid body, due to drag applied by the cylinder wall. The sedimentation or buoyancy of the particles is countered by the continuously changing gravity vector, causing the particles to trace a circular orbit with centers displaced from the axis of rotation. The above-referenced paper by Fowlis and Kornfeld calculates the optimal rotation rate as a function of the many variables, including particle and fluid densities, Reynolds and Taylor numbers associated with the fluid, and the vessel diameter.

U.S. Pat. No. 5,330,908 (Spaulding) discloses a culture vessel for growing mammalian cells constructed in a one piece integral configuration with an opening that is closed by an end cap. This culture vessel is rotatable horizontally about its longitudinal axis using a conventional roller system. The open end has a tapered access port to receive the ends of a hypodermic syringe. Such syringes enable the introduction of fresh nutrient and the withdrawal of spent nutrients.

U.S. Pat. No. 6,387,077 (Klibanov et al.) discloses a syringe pump that suspends particles as the syringe barrel is either intermittently or continuously revolved in a planetary orbit about an axis of rotation that is parallel to the syringe barrel axis. This apparatus is used to introduce biomedical contrast imaging agent into the vascular system of a patient for imaging tissue or organs. In this application, it is advantageous for the agent to be uniformly suspended and injected to achieve improved image quality. In an alternative configuration, a motor is used to both inject and rotate a syringe barrel inside an outer cylindrical housing. While the syringe pump disclosed in U.S. Pat. No. 6,387,077 enables the contents of a syringe to be agitated, the syringe pump does not provide either the desired low pulsatility or rapid reloading capability. It would thus be desirable to provide a syringe pump offering delivery with low pulsatility, which can be rapidly reloaded, and which enables a uniform suspension of cells, beads, or other particles of interest in a sample fluid.

SUMMARY OF THE INVENTION

One aspect of the present invention is directed to a syringe pump that can be operated in a first mode to enable a small volume of fluid to be delivered with low pulsatility, and a second mode in which the syringe can be refilled more rapidly than could be achieved if the syringe pump were operated in the first mode. It should be understood that fluid reservoirs including a fluid displacement piston, plunger, or actuator other than a syringe can be similarly employed, thus the present invention is not limited to the use of a syringe as a fluid reservoir.

In one embodiment, the syringe pump includes a syringe with a plunger and a fluid reservoir, such that a linear displacement of the plunger in a first direction displaces fluid from the fluid reservoir, whereas a linear displacement of the plunger in an opposite direction enables a fluid to be drawn into the fluid reservoir. A driven mass is disposed immediately adjacent to the plunger, such that a linear displacement of the driven mass imparts a corresponding linear displacement to the plunger, the driven mass being configured to convert a rotational displacement to a linear displacement. A driven shaft is configured to engage the driven mass, such that an axial rotation of the driven shaft results in a corresponding linear displacement of the driven mass. Preferably the driven shaft is a precision machined lead screw. The syringe pump includes a transmission operably coupled to the driven shaft, the transmission enabling the driven shaft to be selectively rotated using at least one of a first drive ratio and a second drive ratio. The first drive ratio is substantially higher than the second drive ratio, such that selection of the first drive ratio enables operation of the syringe pump in a first mode. In the first mode, the plunger is moved relatively slowly to accurately dispense small volumes of a fluid. Selection of the second drive ratio enables operation of the syringe pump in the second mode, wherein the plunger is moved relatively quickly to load a fluid into the syringe pump more rapidly than the fluid is dispensed in the first mode. The syringe pump also includes a fluid dispensing motor having a drive shaft. The drive shaft is operably coupled to the transmission so that a rotation of the drive shaft results in a corresponding rotation of the driven shaft, based on the drive ratio of the transmission that is selected.

In a similar embodiment, low pulsatility is achieved by employing a duplex set bearing between a drive train and a threaded lead screw. The threaded lead screw and a correspondingly threaded driven mass are employed to convert a rotational motion of a driven shaft to a linear displacement of the driven mass. As the driven mass is linearly displaced, it moves the piston of the syringe. Preferably, the drive train includes speed reduction with a relatively high drive ratio, so that a drive shaft must be rotated a substantial number of times to achieve a single rotation of the threaded lead screw. In at least one embodiment, the drive ratio is 44:1. The prime mover rotating the drive shaft is preferably a stepper motor with a high number of steps per rotation, enabling precise control over the delivery of small volumes of fluid to be achieved. A preferred motor includes at least 400 discrete steps per rotation. A transmission is beneficially incorporated into the syringe pump, so that the speed reduction can be bypassed in a syringe loading mode, and the syringe can be reloaded more rapidly than it can be emptied. An outlet of the syringe is adapted to be placed in fluid communication with a flow imaging cytometer.

In at least one embodiment, an additional syringe motor and a rotatable syringe support are provided to enable the barrel of the syringe to be rotated about its horizontal axis, independently of the motion of the plunger. Preferably, the syringe pump includes a controller configured to control operation of the fluid displacement motor, the syringe motor, and the transmission. The controller is configurable to rotate the syringe barrel for a predefined period of time before the plunger is linearly displaced to dispense a fluid, to achieve a uniformly distributed sample. In one embodiment, rotation of the syringe barrel does not occur continuously during dispensing of fluid, but is repeated regularly during dispensing, to counter sedimentation and cell aggregation.

In one embodiment, the syringe is continuously rotated at a rate that enables solid body rotation, such that objects entrained in the fluid in the syringe trace substantially circular pathways. Preferably, the rate of rotation is between about one revolution per minute and about ten revolutions per minute, and most preferably, is about three revolutions per minute. In other embodiments, the syringe is rotated before fluid is dispensed and then periodically, as required during the dispensing process.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
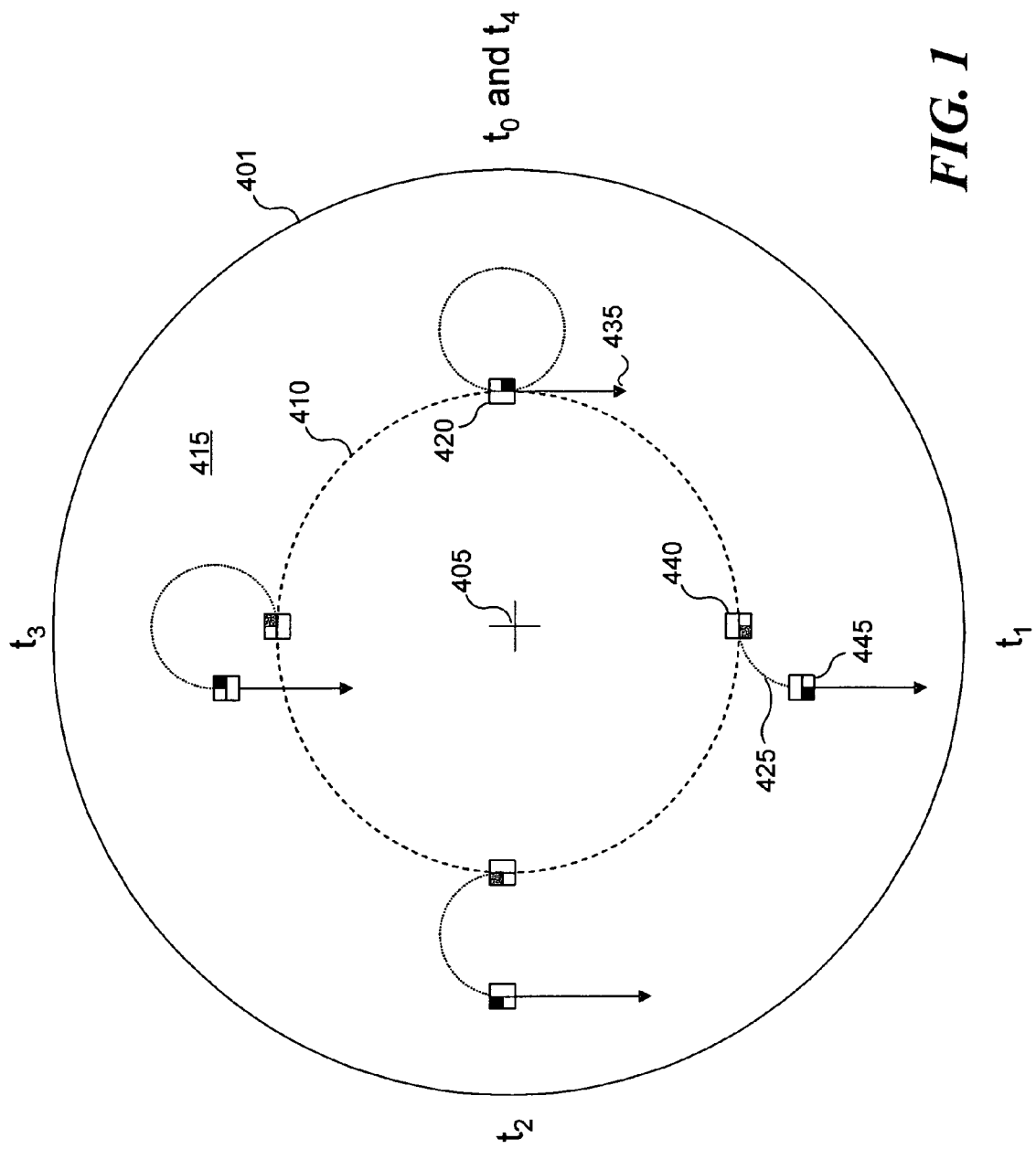
FIG. 1 is a schematic view of the cross-sectional area of the syringe and an orbital trace of a particle during the rotation of the syringe barrel.

Several preferred embodiments of the present invention are described below. In a first preferred embodiment, a low pulsatility syringe pump includes a duplex bearing and a transmission enabling the selection of either a fluid dispensing mode or a refill mode. In this embodiment, the syringe is not rotated. Such a syringe pump is particularly well suited to provide a flow of sheath fluid to the ImageStream™ system discussed above. A second preferred embodiment of the low pulsatility syringe pump includes a duplex bearing and a transmission also enabling the selection of the fluid dispensing mode and the refill mode noted above, but in this embodiment, the syringe is rotated. Such a syringe pump is particularly well suited to provide a flow of a core fluid to the ImageStream™ system discussed above. Preferably, the core fluid will include at least one of sample particles (often biological cells) and calibration beads.

In the second preferred embodiment, it is particularly desirable for the rotation of the syringe barrel to achieve solid body rotation of the contents of the syringe. Such rotation is described in detail below in connection with FIG. 1, which illustrates the orbit traces that a particle undergoes as the syringe barrel is rotated about a longitudinal axis 405 of the syringe barrel. An assumption in this illustration is that a cylinder 401 corresponding to the syringe barrel has been turning continuously and slowly such that an entrained fluid 415 rotates with the syringe barrel much as if the fluid and the barrel were a solid, but with the particles still free to move within the fluid. At a time $t_0$, a particle 420 experiences a gravity vector 435, as depicted by the arrow. At a time $t_1$, a particle 445 has rotated clockwise with the barrel of the syringe and has followed a quarter circular orbital path 425 from its original position 440. The quarter circular shape of the particles trace is due to the continuously changing gravity vector relative to the particle orientation. As the syringe barrel continues to rotate through $t_2$, $t_3$, and $t_4$, the particle returns to the original position tracing out a circular orbit. Note, this orbit assumes that the particle density is greater than the surrounding bulk media, as is the case for cells in a surrounding aqueous based buffer solution. If the particle is less dense, the traced orbit would be offset towards the inside of a median line 410 in the cross section of the syringe. It has been empirically determined in a prototype of the present invention that rotational rates for the syringe barrel of between about one revolution per minute and about ten revolutions per minute provide good results, with about three revolutions per minute being particularly preferred.

Several techniques can be employed to verify that a selected rotational rate achieves the desired solid body rotation (i.e., the circular path illustrated in FIG. 1). Colored particulates can be added to a clear liquid, and placed in a syringe with a transparent barrel. The barrel is then rotated at various rates and the colored particulates are observed, until a rotational rate that enables solid body rotation is identified. Another technique for verifying that a particular rotational rate provides uniform distribution of particles within a fluid is to select a rate, rotate a syringe (or similar fluid reservoir) filled with a fluid using that rate for a period of time, and then analyze the entire volume of the fluid in the syringe using an analytical method that can detect the distribution of entrained particles. If the distribution of particles detected is constant over time for the entire volume of fluid, it can be concluded that the distribution of the particles in the fluid was substantially uniform. An uneven distribution would indicate a non-uniform distribution, and a new rotational rate would be selected, and the process repeated until a substantially uniform distribution is achieved.

For syringe pumps, in accord with the present invention where rotation of the syringe barrel is desired to achieve a uniformly distributed sample, rotation of the syringe barrel can be controlled in a variety of ways. Preferably, the rate of rotation enables solid body rotation as described above. The rotation can be performed for a predefined period of time before the pump begins to dispense fluid. Rotation can be continuous during fluid dispensing, or the rotation can be stopped during fluid dispensing. If it is desired to not rotate the syringe barrel continuously, then periodically during dispensing (or during an interruption of dispensing), rotation of the syringe barrel can be carried out to minimize sedimentation and non-uniform sample distribution during dispensing.

As described above, for any given pump, empirical testing can be performed to determine whether a selected dispensing profile that includes periods of rotation and periods of non rotation achieves a uniform distribution of the sample, and the periods adjusted as necessary.

The ImageStream™ system discussed above can be configured to either use one or more low pulsatility syringe pumps in accord with the present invention. One pump is preferably used to inject the sample containing the objects entrained in a fluid (preferably biological cells) to be imaged. Optionally, an additional pump, which may also be in accord with the present invention, can be used to inject a known size distribution and concentration of micro spheres to enable reference/calibration calculations to be performed on these known/standard objects. The use of such calibration objects is more fully described in commonly assigned and copending U.S. patent application Ser. No. 10/348,193, titled "METHODS OF CALIBRATING AN IMAGING SYSTEM USING CALIBRATION BEADS," the drawings and specification of which are hereby specifically incorporated herein by reference. Preferably, calibration beads and samples are introduced into the flow imaging system described above (i.e. the ImageStream™ system) using a low pulsatility syringe pump that includes syringe rotation capabilities, in accord with the present invention.

Syringe pumps in accord with the present invention, regardless of whether rotation of the syringe barrel is implemented, achieve accurate dispensing and low pulsatility at least in part by employing a duplex bearing set, and a relatively high drive ratio for the fluid dispensing mode. Preferably, a 44:1 drive ratio (speed reduction) is implemented between the stepper motor and the threaded lead screw when the syringe is in the fluid dispensing mode, such that the stepper motor rotates forty-four times per one rotation of the lead screw. Preferably, a stepper motor having 400 steps per rotation is used, where each step is made up of 256 micro steps. Given the preferred 44:1 drive ratio, the 400 steps per rotation of the stepper motor shaft, and the 256 micro-steps per step, this configuration provides 4,505,600 micro steps per each rotation of the lead screw, enabling high precision control of fluid velocity. Because the lead screw has 40 threads per inch or linearly displaces the syringe plunger 0.025 inches (6.35 mm) per rotation, a single micro step results in a linear displacement by the syringe plunger of 0.141 nanometers.

This extraordinary number of micro steps per rotation of the lead screw allows for precise control of the velocity of fluid injected into the cuvette, which is ideal for a sample injection. However, for drawing a sample of fluid into the syringe (or to aspirate a load from the syringe), this precise control movement of the syringe plunger results in an excessive time to load or aspirate the syringe. For this reason a transmission is included that enables the drive ratio to selectively be changed from 44:1 to 1:1 in order to increase the speed at which the plunger can be displaced for sample loading and unloading, where precise control of fluid dispensing is not required.

The use of a duplex bearing set enables a rigid, or low compliance, fluid dispensing pump to be achieved. It has been empirically determined that low compliance units inherently achieve fluid delivery with lower pulsatility than can be achieved with less rigid units. In the present invention, the combination of a rigid unit including a duplex bearing set with a micro stepper motor and a reducing transmission enables precisely controlled low volume fluid delivery to be achieved with minimal pulsatility.

Details of the first preferred embodiment of a low pulsatility syringe pump in accord with the present invention are discussed below, in conjunction with FIG. 2. Details of the second preferred embodiment of a low pulsatility syringe pump enabling rotation of the syringe barrel are discussed below, in connection with FIGS. 3 and 4.

Figure 2:
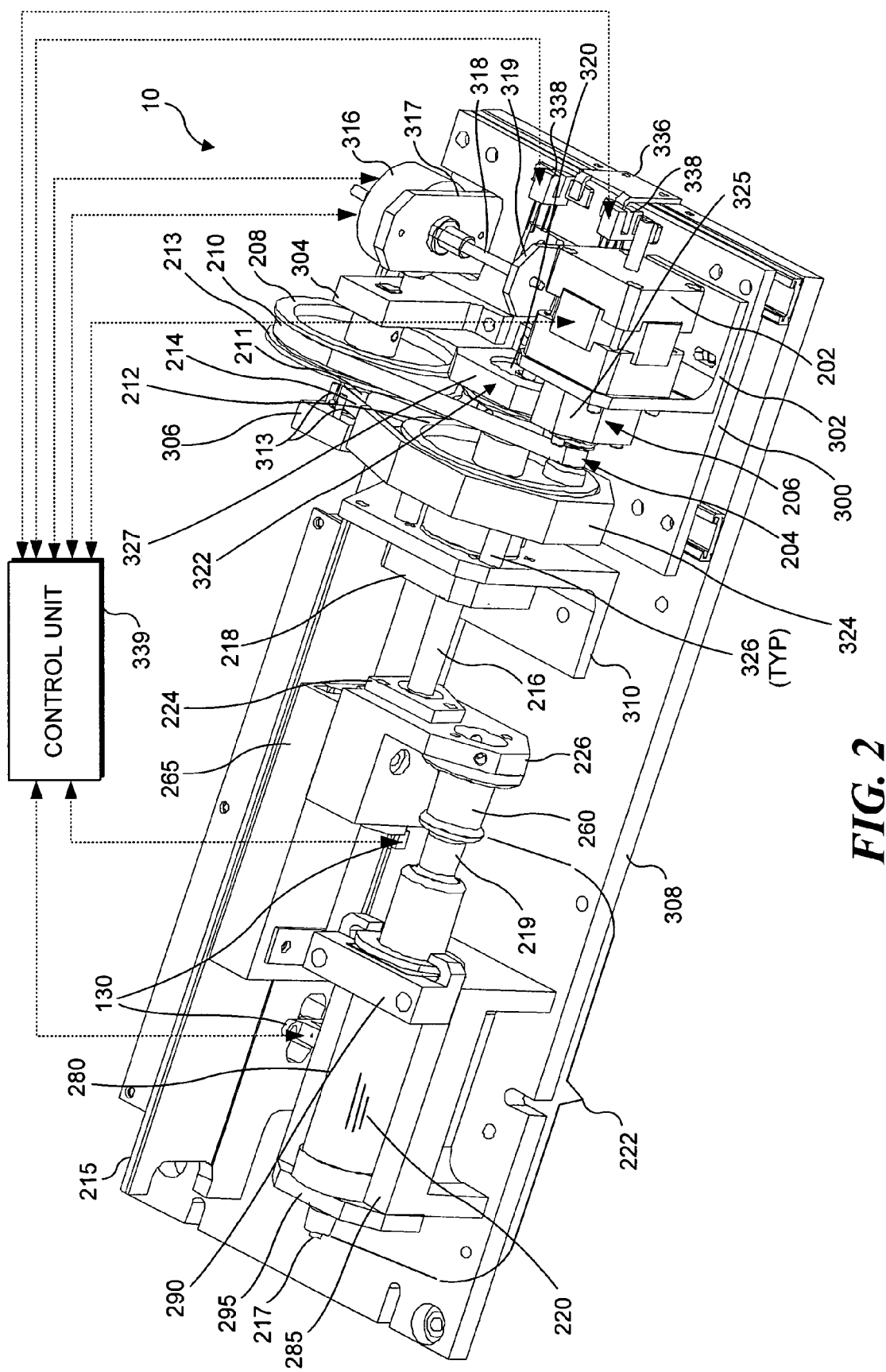
FIG. 2 is an isometric view of a first embodiment of a low pulsatility syringe pump in accord with the present invention in which rotation of the syringe barrel is not enabled.
Figure 3:
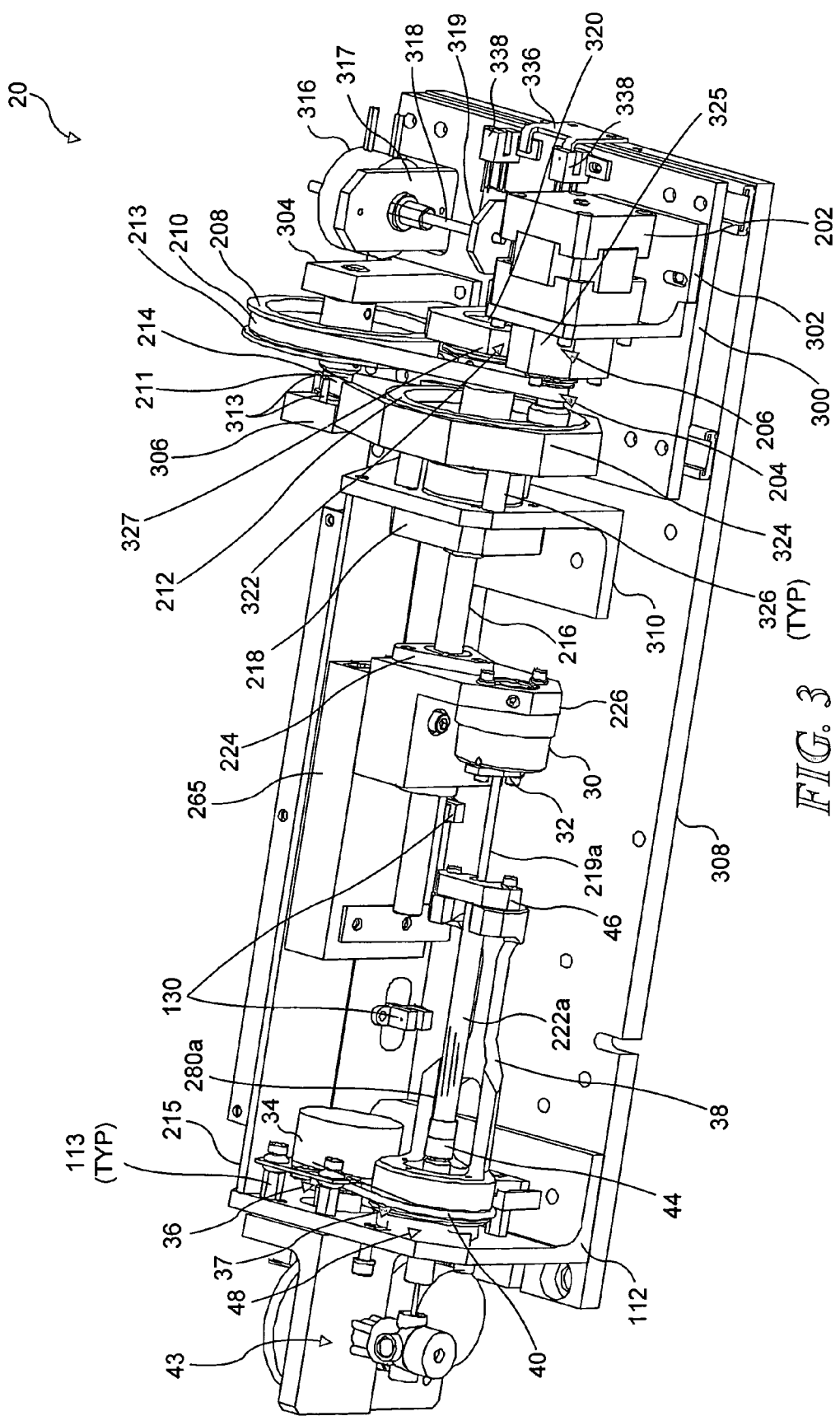
FIG. 3 is a first isometric view of a second embodiment of a low pulsatility syringe pump in accord with the present invention in which rotation of the syringe barrel is enabled.
Figure 4:
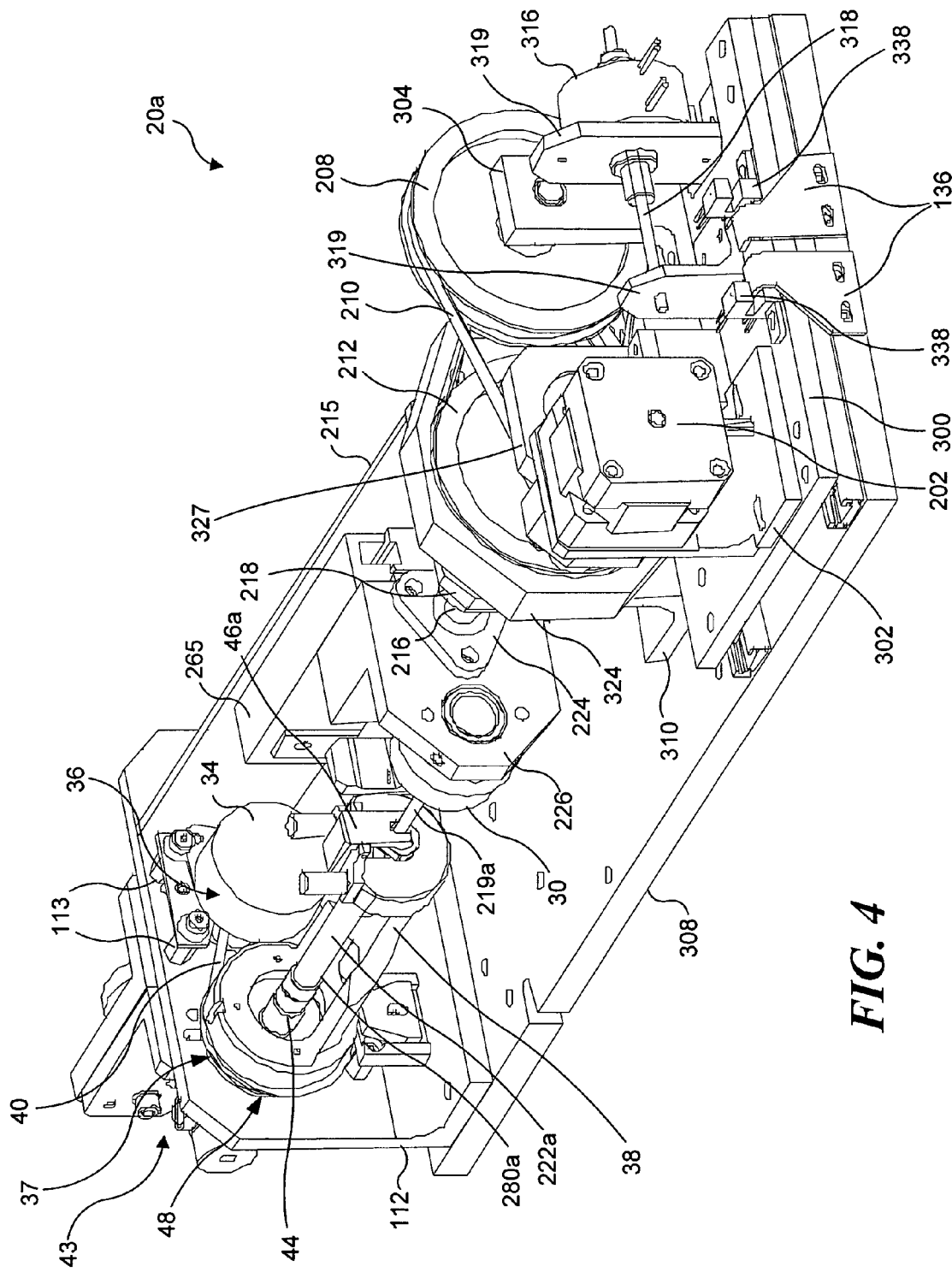
FIG. 4 is a second isometric view of the second embodiment of a low pulsatility syringe pump in accord with the present invention.

FIG. 2 is an isometric view of the first preferred embodiment of the present invention, showing a syringe pump 10 including a duplex bearing to enable low pulsatility to be achieved, and a two speed transmission. It should be noted that the syringe pumps shown in FIGS. 2-4 each include a plurality of pulleys and belts that enable motor drive shafts to drivingly couple to driven elements. FIGS. 2-4 are shown with the belts in place, which partially or completely obscures some of the related pulleys. It should be understood that working models of syringe pumps in accord with the present invention require such belts to be appropriately positioned on their respective pulleys. It should also be understood that rather than using the pulley/belt configurations illustrated, a plurality of gears of appropriate size can instead be employed to drivingly couple the motor drive shafts to their respective driven elements. Thus, the pulley/belt configurations shown and discussed below should be considered an exemplary implementation, rather than limiting on the scope of the present invention.

Referring now to FIG. 2, a micro stepper fluid displacement motor 202 has two pulleys 204 and 206 attached to the motor's drive shaft. Note that pulleys 204 and 206 are obscured from view, and their approximate locations are indicated by arrows. As the micro stepper fluid displacement motor is stepped, pulley 204 rotates transmitting driving force through a timing belt 210 to rotate an idler pulley 208. Preferably the drive ratio of pulleys 204 and 208 is 15:100. As idler pulley 208 rotates, so does a smaller idler pulley 211 (pulley 208 and pulley 211 being coupled to a common shaft—not separately shown). An injection timing belt 214 drivingly couples smaller idler pulley 211 to an injection lead screw pulley 212, causing the injection lead screw pulley to turn. Preferably, the drive ratio of idler pulley 211 and pulley 212 is also 15:100. The injection lead screw pulley 212 turns a threaded lead screw 216 (having the above mentioned 40 threads per inch) within a duplex bearing set 218, which is supported by a support 310 fixedly attached to a base 308.

As injection lead screw 216 rotates within duplex bearing set 218, its thread engage the threads of a lead screw nut 224, converting the rotation of the lead screw into a linear displacement of the lead screw nut. Lead screw nut 224 is coupled to a driven mass 226, which in turn is coupled to a syringe plunger 219 via a spacer 260. The linear displacement of lead screw nut 224 thus causes a linear displacement of syringe plunger 219 within the fluid reservoir of a syringe 222. Movement of syringe plunger 219 into the syringe forces a fluidic suspension 220 out of syringe 222.

Note that driven mass 226 is guided by a slide carriage 265, which slidingly engages a support bracket 215 coupled to base plate 308. Slide carriage 265 and support bracket 215 greatly increase the rigidity of the pump, which has the advantage of reducing a pulsatility with which fluid is delivered. A single screw is used to secure syringe plunger 219 to spacer block 260. A syringe barrel holder 285 coupled to base plate 308, supports syringe barrel 280. A top barrel clamp plate 290 and an end barrel clamp plate 295 are coupled to syringe barrel holder 285, to hold syringe barrel 280 in place in all axes.

As noted above, each of the two particularly preferred embodiments (the non rotating syringe pump of FIG. 2, and the rotating syringe pump of FIGS. 3 and 4) preferably each include a transmission having a speed reducing drive for precise control of fluid delivery, and an additional drive speed enabling more rapid filling and aspiration of the syringe. The transmission in each embodiment is substantially the same, and a preferred transmission will now be described in detail. Micro stepper fluid displacement motor 202 is attached a sliding plate 300 via a motor bracket 302. Idler pulley 208 is rotatably supported on its shaft, and the shaft is coupled to sliding plate 300 via two hanger shaft mounts 304 and 306. Pulley 206 (obscured from view by a pulley cover 325) and pulley 204 are driven by the drive shaft of micro stepper fluid displacement motor 202. A belt 322 (obscured from view) drivingly couples pulley 206 to a pulley 320 (mostly obscured from view by a pulley cover 327), depending on the which drive train is engaged by the transmission. While lead screw nut 224 is coupled to a first end of lead screw 216, pulley 320 is coupled to the opposite end of lead screw 216 (it should be understood that an alternative configuration would be for lead screw 216 to be drivingly coupled to a driven shaft that is coupled to lead screw 216). Thus, lead screw 216 can be drivingly rotated by either pulley 320 or pulley 212. Neither pulley 320 nor pulley 212 is coupled to sliding plate 300. The position of sliding plate 300 determines which of pulleys 320 and 212 drivingly rotates lead screw 216. When sliding plate 300 is in a first position, a first drive train including pulley 204, belt 210, pulley 208, pulley 211, belt 214, and pulley 212 is engaged. Note this first drive train is a reduction drive, so that many rotations of the drive shaft of micro stepper fluid displacement motor 202 are required to produce each rotation of lead screw 216. The first drive train is employed to achieve greater control over the delivery of small volumes of fluid. When sliding plate 300 is in a second position, a second drive train including pulley 206, belt 322, and pulley 320 is engaged. The second drive train does not include the speed reduction of the first drive train (or if any speed reduction is included, it is minimal). The second drive train is included to enable the syringe to be emptied or reloaded at a rate that is faster than could be achieved using the first drive train.

The position of sliding plate 300 is selectively set by a transmission motor 316, which serves as a transmission actuator control and is supported by a bracket 317. Bracket 317 is fixedly attached to base 308. A drive shaft 318 of transmission motor 316 is threaded into corresponding threads in a bracket 319, which is fixedly attached to sliding plate 300. Thus, transmission motor 316 is used to move the sliding plate between the first and second positions. Note that when the first drive train is engaged (pulley 204, belt 210, pulley 208, pulley 211, belt 214, and pulley 212), belt 322 tension associated with the second drive train (pulley 206, belt 322, and pulley 320) is reduced to prevent any driving force between pulleys 206 and 320. Similarly, when the second drive train is engaged, belt 214 tension is reduced to prevent transmitting driving force between pulleys 211 and 212. Belt 210 remains taught in both drive positions (note that pulleys 204 and 208, which engage belt 210, each move in conjunction with sliding plate 300). The position of sliding plate 300 thus controls the drive train that is engaged.

Preferably, belt restrainers and pins are included to prevent the belts from engaging their pulleys when the belts are not taut. Pulley 206 is covered by belt restrainer 325, which is positioned such that belt 322 will not engage pulley 206 when belt 322 is not taut. Pulley 320 is similarly covered by pulley cover 327, which is positioned such that belt 322 will not slip off pulley 320 when belt 322 is not taut. Belt restrainer 327 is fixedly coupled to base plate 308, and sliding plate 300 includes a cut out shaped so that belt restrainer 327 allows the sliding plate to moving back and forth between the first and second positions. Pulley 208 includes flanges 213 that extend sufficiently outward so that belt 210 will not slip off pulley 208. A plurality of pins 313 extend outwardly from support 306 to restrain belt 214 from engaging pulley 211 when belt 214 is relaxed. Belt restrainer 324 prevents belt 214 from engaging pulley 212 when belt 214 is relaxed. Belt restrainer 324 is coupled to support 310 via a plurality of standoffs 326.

To aid in controlling the position of sliding plate 300 and lead screw 216 (and thus plunger 219), a microprocessor-based control unit 339 is controllably coupled to micro stepper fluid displacement motor 202 and transmission motor 316. It should be understood that other types of controllers, such as hard-wired logic devices or application specific integrated circuits (ASICs), can be utilized to implement control functions in the present invention. Optical position switches 338 (logically coupled to control unit 339) are coupled to sliding plate 300, and a shutter 336 is coupled to base plate 308, enabling the position of sliding plate 300 to be accurately determined and controlled. While obscured from view in FIG. 2, it should be understood that a pair of optical position switches 130 (logically coupled to control unit 339) are coupled to bracket 215 (which is fixedly coupled to base plate 308) and a shutter (obscured from view syringe support 285) attached to slide carriage 265 similarly enable the position of slide carriage 265 (thus lead screw 216 and plunger 219) to be accurately determined and controlled. Control unit 339 is programmed to operate the syringe pump according to pre-defined operation profiles, such that fluid is dispensed at a desired rate. Control unit 339 can be programmed to initially fill the syringe (using the second drive train described above), to then dispense a desired volume of fluid (using the first drive train described above), and then once again refill the syringe (using the second drive train described above), repeating these steps in sequence as required. A preferred use for syringe pump 10 is to provide a flow of sheath fluid to a flow imaging cytometer. In such an application, an outlet 217 of syringe 222 would be coupled in fluid communication with a flow imaging cytometer, such as the systems described in the above-referenced commonly assigned patents.

As noted above, a second preferred embodiment of a fluid dispensing device in accord with the present invention is a syringe pump configured to rotate the syringe barrel about its own axis, independently of the delivery of fluid from the syringe. FIG. 3 is an isometric view of a syringe pump 20 corresponding to this second embodiment. FIG. 4 is an isometric views of a syringe pump 20a, which is the functional equivalent to syringe pump 20, but includes minor structural differences that are discussed in detail below. It should be understood that the drive trains and transmissions of syringe pumps 20 and 20a are functionally and structurally identical to the drive train and transmission in syringe pump 10. The significant functional and structural difference between syringe pump 10 and syringe pumps 20 and 20a are the elements required to enable rotation of the syringe in syringe pumps 20 and 20a.

While a control unit is not shown in FIG. 3 or 4, a control unit implementing the functions described above in connection with syringe pump 10, will also preferably be used to control syringe pump 20 or 20a. FIGS. 3 and 4 include fluid control elements 43 configured to direct and control a flow of fluid dispensed from the syringe when the plunger is manipulated. Those of ordinary skill in the art will readily recognize that depending on how a fluid dispensed from syringe pump 20 or 20a is to be utilized, many different configurations of fluid control elements can be employed to utilize and direct the flow of fluid dispensed from the syringe pumps. Accordingly, fluid control elements 43 are not discussed in detail. It should also be noted that a syringe 222a, a syringe barrel 280a, and a syringe plunger 219a shown in FIGS. 3 and 4 are slightly different than the corresponding elements shown in FIG. 2. An exemplary application for syringe pump 10 is to provide a sheath fluid for an imaging flow cytometer, while an exemplary application for either syringe pump 20 or syringe pump 20a is to provide a sample fluid for use with the sheath fluid, in an imaging flow cytometer system. In such applications, a larger volume of sheath fluid than sample fluid is required, so that a larger syringe is shown in connection with syringe pump 10. Those of ordinary skill in the art will readily understand that with minor modifications to the syringe support elements, syringe pumps 10, 20, and 20a can be utilized with syringes of varying sizes. Thus, the syringes illustrated in FIGS. 2-4 should not be considered limiting on the scope of the present invention.

As discussed above, syringe pump 20 enables the barrel of the syringe to be rotated independently of the movement of the plunger. For example, the syringe barrel can be rotated for a period of time before the plunger is moved to dispense any fluid to ensure that all particulates entrained within the fluid are uniformly distributed in the fluid. The rotation need not be implemented continuously during fluid dispensing, although if desired, a continuous rotation can be supported. If rotation is not performed continuously during fluid dispensing, it may be desirable to rotate the syringe barrel after a defined interval of time, such that particles remain substantially uniformly distributed during an extended dispensing cycle. Preferably, empirical tests are performed to determine how frequently the syringe barrel must be rotated during a given dispensing cycle to ensure that particles entrained in the fluid remain substantially uniformly distributed throughout the fluid in the syringe barrel.

The structural and functional elements of syringe pump 20 that enable rotation of the syringe barrel will now be discussed, in regard to FIG. 3. A mounting pad 30 is coupled to driven mass 224, to rotatably support syringe plunger 219a. The syringe rotation assembly includes a syringe rotation stepper motor 34 having an output shaft (not shown) to which a pulley 36 is attached. A belt 40 drivingly couples pulley 36 to a pulley 37, which is either integral with or fixedly attached to a syringe barrel cradle 38. The syringe barrel cradle serves to support syringe barrel 280a, both at a luer lock fitting 44 and at the plunger end of the barrel via a barrel swing clamp 46. Syringe barrel cradle 38 is rotatably supported by a bearing 48, and bearing 48 is supported by a bracket 112, which in turn is fixedly attached to base plate 308. Note that syringe rotation stepper motor 34 is attached to bracket 112 using standoffs 113. Preferably, support bracket 215 (which slidingly supports slide carriage 265) is coupled to both brackets 112 and 310, to provide extra rigidity to the structure of syringe pump 20.

The precision with which plunger 219a of syringe pump 20 can be laterally translated (approximately 5 nanometers per step of micro stepper fluid displacement motor 202 in a current implementation) can be defeated if the rotational axis of the syringe barrel cradle 38 is not precisely aligned with mounting pad 30. Any wobble motion with respect to the rotation of syringe barrel cradle 38, will result in an axial oscillation of plunger 219a. Such oscillation will introduce undesirable pulsatility in the flow rate. Bearing 48 and bracket 112, which supports bearing 48, preferably are precision components that are preloaded when assembled so as to eliminate slop. Additional configurations, including incorporating an additional bearing and support structure proximate barrel swing clamp 46 can also be employed, so long as such configurations minimize wobble associated with respect to the rotation of syringe barrel cradle 38.

A similar flow pulsatility issue can be introduced by wobble if a bearing is installed in mounting pad 30. Therefore, a syringe whose barrel is free to rotate independently of the plunger is employed. When such a syringe is utilized, no bearing is included in the mounting pad, and the plunger is not rotated, just as implemented in syringe pump 10 of FIG. 2.

The rotation of pulley 37 by belt 40 (driven by pulley 36 coupled to the drive shaft of stepper motor 34) will impart some measurable force on the syringe and may introduce additional wobble in the rotation of the syringe, which as described above, is undesirable. Pulsatility caused by such forces can be eliminated by rotating the syringe rarely, or not at all, when the plunger is being linearly displaced. As discussed above, syringe pump 20 can be operated according to a dispensing profile in which the syringe is rotated each time before the fluid is dispensed to ensure uniform distribution of entrained particles, but only rarely (or not at all) when the plunger is being linearly translated to dispense the fluid. A control unit (such as control unit 339) can be configured to stop the linear translation of the plunger when the syringe is being rotated. In some applications, such temporary interruptions of fluid dispensing are acceptable. In applications where even temporary interruptions of fluid delivery are unacceptable, a control unit can be configured to rotate the syringe during dispensing only periodically, at time intervals that are based on empirical testing. Such testing can determine a minimum duration of rotation during dispensing that will achieve an acceptable distribution of entrained particles. Yet another technique to reduce pulsatility introduced by stepper motor 34 is to select a modulation amplitude and phase of stepper motor 34 that correspond to the frequency of rotation of the syringe, to minimize any pulsatility that may be introduced by the rotation.

FIG. 4 illustrates syringe pump 20*a* that has been slightly modified from syringe pump 20 of FIG. 3. Shutter 336, which was formed as a single piece in syringe pump 20, is replaced with a two part shutter 136 in syringe pump 20*a*. Barrel swing clamp 46 of syringe pump 20 is replaced with a slightly modified barrel swing clamp 46*a* in syringe pump 20*a*. The other functional and structural elements of syringe pump 20*a* remain the same as in syringe pump 20.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention claimed is:

1. A method for dispensing a fluid containing substantially uniformly distributed particulates entrained therein, comprising the steps of:
   (a) providing a container having a longitudinal axis, the container including a volume of fluid in which is entrained a plurality of particulates;
   (b) rotating the container in which the fluid is disposed about its longitudinal axis using a rate of rotation that results in the fluid, the particulates in the fluid, and the container achieving solid body rotation, wherein the container is rotated using a first prime mover; and
   (c) dispensing the fluid independently of rotating the container, such that rotation of the container is not required in order for the fluid to be dispensed, wherein the fluid is dispensed using a second prime mover that introduces a member into the container to displace the fluid.

2. A method for dispensing a fluid containing substantially uniformly distributed particulates entrained therein, comprising the steps of:
   (a) providing a container having a longitudinal axis, the container including a volume of fluid in which is entrained a plurality of particulates;
   (b) rotating the container in which the fluid is disposed about its longitudinal axis using a first prime mover and a rate of rotation that results in the particulates in the fluid tracing a substantially circular pathway; and
   (c) dispensing the fluid independently of rotating the container using a second prime mover to manipulate a member introduced into the container to displace the fluid, such that dispensing occurs without requiring the container to be rotating.

3. A method for dispensing a fluid containing substantially uniformly distributed particulates entrained therein, comprising the steps of:
   (a) providing a container having a longitudinal axis, the container including a volume of fluid in which is entrained a plurality of particles, the container including a member configured to dispense fluid from the container when the member is manipulated;
   (b) rotating the container in which the fluid is disposed about its longitudinal axis before dispensing the fluid in the container using a first prime mover, such that the particulates become substantially uniformly distributed within the fluid in the container;
   (c) halting the rotation of the container;
   (d) dispensing the fluid when the container is not rotating using a second prime mover to manipulate the member to displace the fluid; and
   (e) repeating steps (b), (c), and (d).

4. The method of claim 3, wherein the container is rotated at a rate that results in a solid body rotation of the container, the fluid and the particulates entrained within the fluid.

5. The method of claim 3, wherein the container is rotated at a rate that results in particulates entrained within the fluid tracing a substantially circular path.

6. The method of claim 3, wherein the container is rotated at a rate that is between about one revolution per minute and about ten revolutions per minute.

7. The method of claim 3, wherein the container is rotated at a rate of about three revolutions per minute.

8. The method of claim 3, further comprising the step of ceasing dispensing of the fluid from the container before repeating steps (b), (c), and (d).

9. The method of claim 3, wherein the first prime mover used to rotate the container is a motor, and further comprising the step of matching a frequency modulation and phase characteristics of the motor to a rate of rotation of the container, thereby reducing a pulsatility induced in the dispensing of the fluid.

10. The method of claim 3, further comprising the steps of:
   (a) rotating the container about its axis during the step of dispensing the fluid, for a period of time sufficient to enable the particulates to become substantially uniformly distributed within the fluid in the container; and
   (b) halting the rotation of the container.

11. A method for dispensing a fluid containing substantially uniformly distributed particulates entrained therein with reduced pulsatility, comprising the steps of:

(a) providing a container having a longitudinal axis, the container including a volume of fluid in which is entrained a plurality of particles, the container including a member configured to dispense fluid from the container when the member is manipulated;

(b) rotating the container in which the fluid is disposed about its longitudinal axis before dispensing the fluid in the container, such that the particulates become substantially uniformly distributed within the fluid in the container, using a first prime mover whose frequency modulation and phase characteristics are matched to a rate at which the container is rotated, to reduce a pulsatility induced in the fluid;

(c) halting the rotation of the container;

(d) dispensing the fluid when the container is not rotating; and (e) repeating steps (b), (c), and (d).

* * * * *